United States Patent [19]

Bleiweiss

[11] Patent Number: 5,575,776

[45] Date of Patent: Nov. 19, 1996

[54] SINGLE DOSE, PREFILLED, DISPOSABLE SYRINGE

[76] Inventor: Warren J. Bleiweiss, 12 Fox Run, North Caldwell, N.J. 07006

[21] Appl. No.: 552,229

[22] Filed: Nov. 2, 1995

Related U.S. Application Data

[63] Continuation of Ser. No. 350,987, Nov. 29, 1994, abandoned.

[51] Int. Cl.[6] .................................................... A61M 5/00
[52] U.S. Cl. ........................................... 604/187; 604/218
[58] Field of Search ................................... 604/187, 110, 604/218, 192, 263

[56] References Cited

U.S. PATENT DOCUMENTS 1,529,659  3/1925  Marcy ..................................... 604/218
3,642,000  2/1972  Baker ..................................... 604/218

*Primary Examiner*—John D. Yasko
*Attorney, Agent, or Firm*—Hoffman, Wasson & Gitler

[57] ABSTRACT

A single dose, prefilled, disposable syringe is provided in which an outer casing surrounding the syringe in the packaged state is collapsible to act as a plunger during use of the syringe. The outer casing has a series of longitudinal grooves formed around its circumference to facilitate collapsing of the outer casing. The collapsed outer casing has a smaller diameter than the barrel of the syringe so that the collapsed outer casing can push the piston through the barrel of the syringe to eject the single dose of medication.

14 Claims, 3 Drawing Sheets

SINGLE DOSE, PREFILLED, DISPOSABLE SYRINGE

This application is a continuation of application Ser. No. 8/350,987 filed on Nov. 29, 1994 now abandoned.

FIELD OF THE INVENTION

The present invention pertains to a single dose, prefilled, disposable syringe. More particularly, the syringe contains a predetermined dose of a pre-chosen drug and is intended to be capable of only a single use. A protective outer casing, which surrounds the syringe prior to use, is collapsed after removal so that it can be used as a plunger in the syringe.

BACKGROUND OF THE INVENTION

With the increase in the spread of infectious diseases, and in particular the risk of infection due to repeated use of hypodermic needles, it is desirable to create a syringe which can be used only a single time. Various syringes exist which allow the user to break off the needle once the syringe has been used. However, until someone chooses to break off the needle of such a syringe, it is possible to reuse the syringe.

Other single dose syringes exist, in particular, the ABBOJECT made by Abbott Laboratories, which employs a vial and an injector. Both the vial and the injector have caps on one of their ends. The vial has a small enough outer diameter that it can fit into the inner diameter of the injector. Once the vial is inserted into the injector and rotated clockwise a specific number of turns, the medication will enter the needle, whereupon the needle cover is removed, and the device is ready for use.

Another single dose device is the TEL-E-JECT device made by the Hoffmann LaRoche Inc. Company. This device employs a plastic plunger which is hollow and fits over a rubber needle cover during transport. The plunger is removed from the rubber needle cover and screwed into a plunger in a plunger barrel containing a dose of a particular drug. Once the plunger is screwed into the piston barrel, the TEL-E-JECT syringe is ready for use.

The aforementioned devices suffer from various drawbacks. In particular, these devices require significant storage space and are complicated to set up. In addition, the TEL-E-JECT device, while providing a single dose in its initial system, can be reused since the plunger screws into the piston, thus allowing the plunger to be pulled back to draw in a second dose of a drug for subsequent delivery.

SUMMARY OF THE INVENTION

The foregoing and other deficiencies of the prior art are addressed by the present invention which is directed to a single dose, prefilled, disposable syringe.

In particular, it is an object of the present invention to provide a single dose, prefilled, disposable syringe which can rapidly deliver premeasured liquid medication, such as for intravenous injection.

Another object of the present invention is to provide a single dose, prefilled, disposable syringe which has convenient storage packaging.

Yet another object of the present invention is to provide a single dose, prefilled, disposable syringe which cannot be reused.

Still another object of the present invention is to provide a single dose, prefilled, disposable syringe in which the ability to draw a medication into the syringe after ejection of the prefilled medication dose is incapacitated.

Yet another object of the present invention is to provide a single dose, prefilled, disposable syringe, in which an outer protective casing can be collapsed upon itself for utilization as a plunger.

BRIEF DESCRIPTION OF THE DRAWINGS

The foregoing and other objects and attributes of the present invention will be described with respect to the following drawings in which.

DETAILED DESCRIPTION OF THE INVENTION

Figure 1:
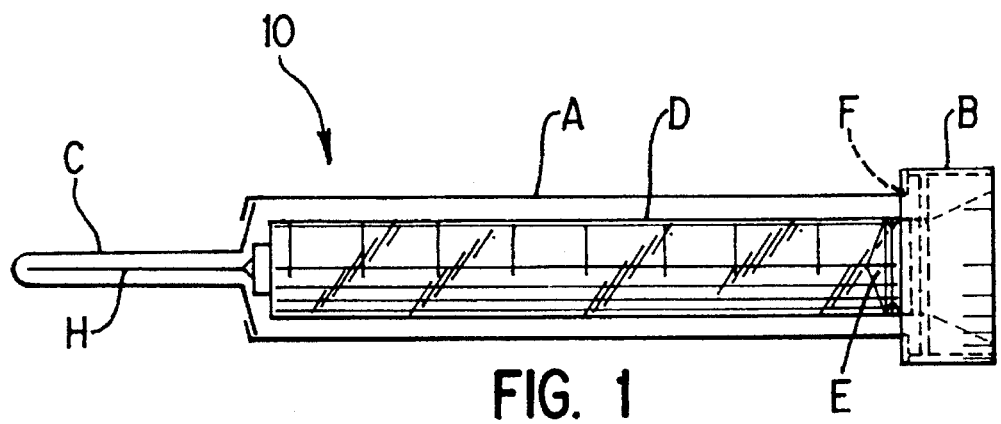
FIG. 1 is a side view of the single dose, prefilled, disposable syringe of the present invention, in its packaged state.

Referring to FIG. 1, a single dose, prefilled, disposable syringe according to the present invention is shown in its packaged state.

The syringe 10 includes a syringe barrel D, a piston E and a needle H. The syringe 10, in its packaged state, is contained within an outer casing A, a protective cover B, which is joined to the outer casing by plastic welds F, and a needle cover C which interlocks with the outer casing A.

Figure 7:
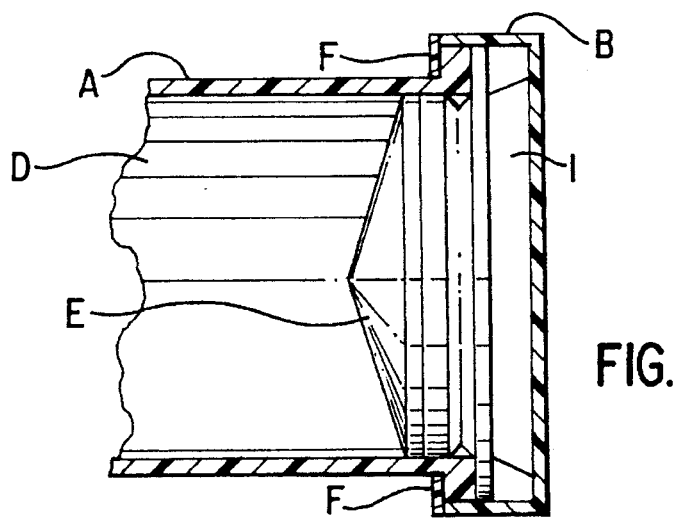
FIG. 7 is a detailed side view of the outer casing as it is attached to a protective cover prior to collapsing.
Figure 8:
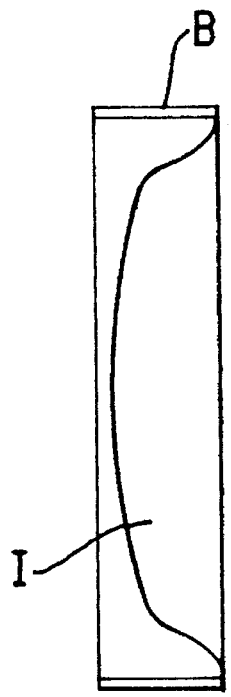
FIG. 8 is a cross-sectional view of the inner ring of the protective cover shown in FIG. 7.

The barrel of the syringe D is filled with a predetermined dose of a drug which is contained by the piston E on one end and the needle H on the opposite end. The outer casing A interlocks with the needle cover C on one end and the protective cover B on the other end. Referring to FIG. 7, the outer casing A is attached to the protective cover B by breakaway plastic welds F. These welds F are designed so that the user can detach the protective cover B from the outer casing A with ordinary hand-applied force, such as by twisting. Referring to FIGS. 7 and 8, while the syringe is in the packaged state, an inner ring I on the protective cover B provides stability in the storage position by fitting into the barrel of the syringe D near the piston E.

Figure 2:
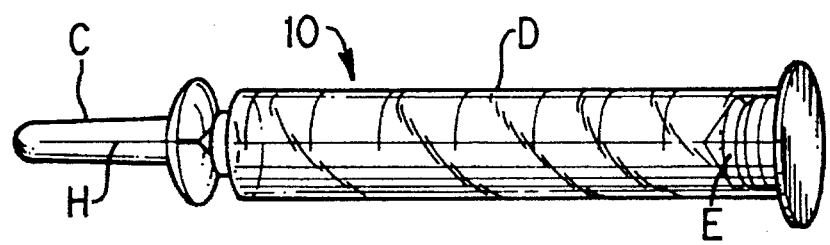
FIG. 2 is a side view of the single dose, prefilled, disposable syringe of the present invention separated from its outer housing.
Figure 2:
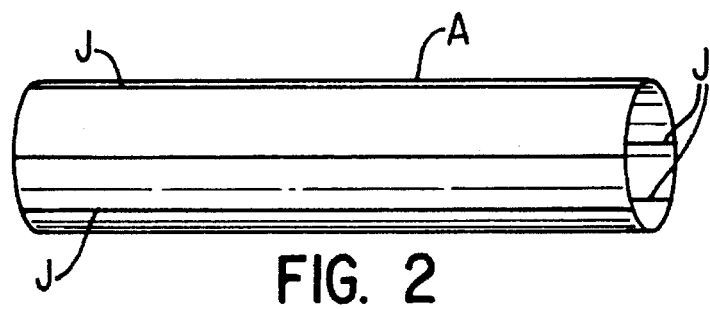
Figure 9:
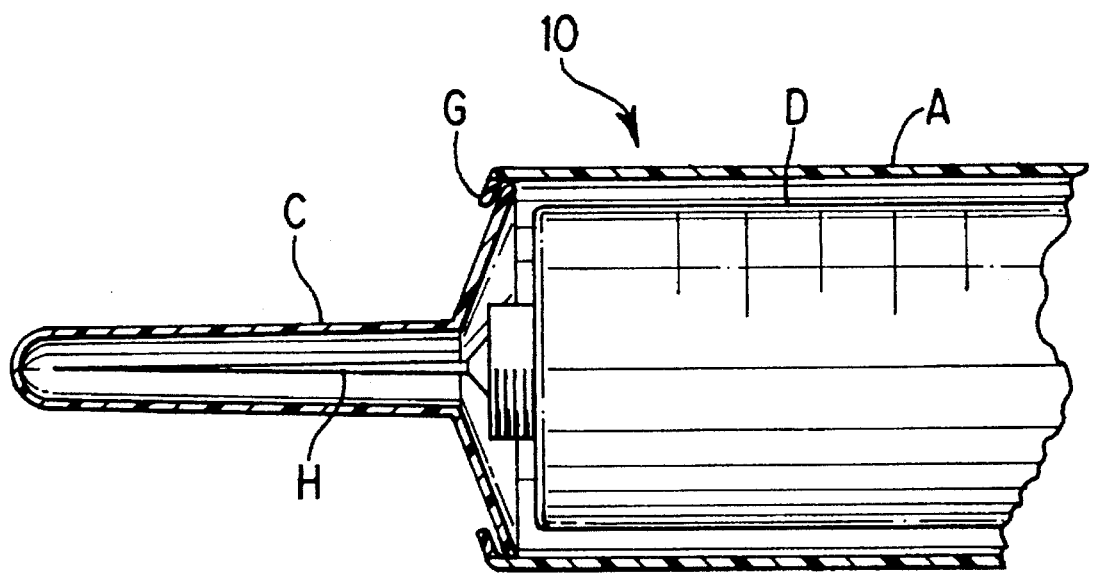
FIG. 9 is a side cross-sectional view of the outer casing and needle cover of the single dose, prefilled syringe of the present invention.

Referring to FIG. 9, the needle cover C, and the outer casing A interlock with one another by flanges or hooks G disposed around the circumferences of each element. The hooks G are held in place by the attachment of the outer casing A to the protective cover B via the plastic welds F, as shown in FIG. 7. Once the outer casing A and protective cover B are detached from one another to break the welds F, the outer casing A and needle cover C can be separated by sliding the outer casing A over the needle cover C. FIG. 2 illustrates a partially unpackaged single dose, prefilled, disposable syringe 10 of the present invention where the outer casing A has been detached from the protective cover B and disengaged from the needle cover C.

Figure 3:
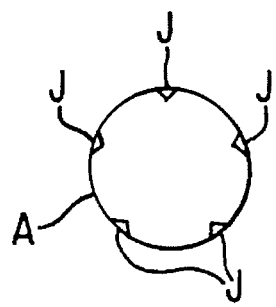
FIG. 3 is a cross-section of the outer housing shown in FIG. 2.

Referring to FIGS. 2 and 3, the outer casing A has a series of grooves J formed therein. In the embodiment shown in FIG. 3, there are five such grooves J spaced at equal distances around the circumference of the outer casing A.

Figure 4A:
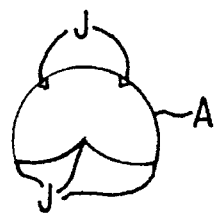
FIGS. 4A and 4B are cross-sections of the outer housing shown in various states of collapse.
Figure 4B:
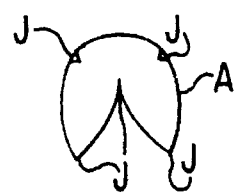

Turning now to FIGS. 4A and 4B, the collapsing of the outer casing A is illustrated. In particular, a user can apply force to the outside of the outer casing A at one of the grooves J so that a portion of the outer casing A inverts upon itself around that chosen groove J. As the outer casing A is collapsed, the remaining surface of the outer casing A bends about the other grooves J to achieve a smaller cross-section as shown in FIG. 4B.

Figure 5:
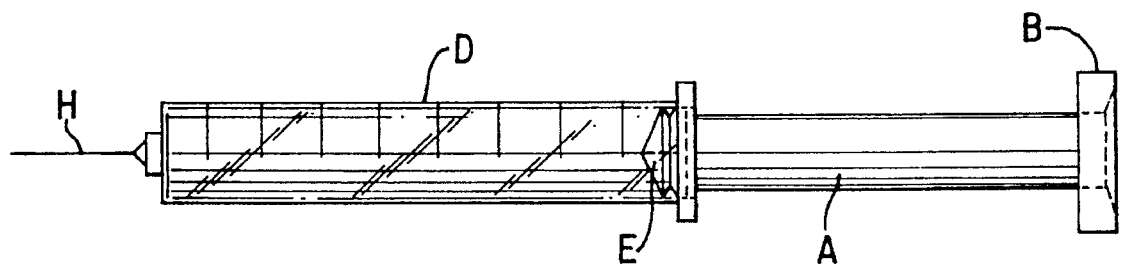
FIG. 5 is a side view of the single dose, prefilled, disposable syringe of the present invention where the collapsed outer casing has been inserted as the plunger.

Once the outer casing A is fully collapsed, the protective cover B can be attached to one end of the collapsed outer casing A, while the opposite end of the collapsed outer casing A is inserted into the plunger E, as illustrated in FIG. 5.

Figure 6:
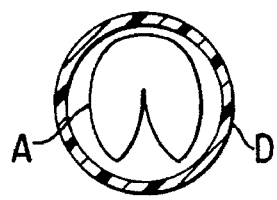
FIG. 6 is a cross-section of the plunger and syringe as shown in FIG. 5.

Referring to FIG. 6, it can be seen that the collapsed outer casing A has a smaller cross-section than the inner diameter of the barrel of the syringe D. Thus, when the plunger, made up of the collapsed outer casing A and protective cover B is depressed, the piston E will move, to the left in FIG. 5 to eject the prefilled medication from the syringe 10.

The collapsed outer casing A does not interlock with the piston E, so that once the medication is ejected from the syringe 10, withdrawal of the plunger will not draw the piston E away from the needle H through the barrel of the syringe D. Consequently, the syringe 10 cannot be used to draw medication into the syringe for a second use. The piston E remains disposed at the end of the barrel of the syringe D nearest the needle H.

The provision of the grooves J around the circumference of the outer casing A allows them to act as plastic hinges so that the outer casing A can be collapsed upon itself when external pressure is applied. Thus, in the packaged state, the outer casing A has a larger diameter than the barrel of syringe D and in the collapsed state has a diameter smaller than the inner diameter of the barrel of the syringe D. The provision of the protective cover B on the end of the collapsed outer casing A as illustrated in FIG. 5 is to provide a greater comfort to the user when depressing the free end of the collapsed outer casing A. In an emergency, when rapid injection is necessary, the user may opt not to attach the protective cover B.

In use, the user would break the plastic welds F by holding the outer casing A with one hand and the protective cover B with the other hand and twisting the two elements in opposite directions to break the plastic welds F. The barrel of the syringe D is then withdrawn by applying pressure to the needle cover C while holding the outer casing A. The outer casing A is then collapsed and placed into the barrel of the syringe D and protective cover B is positioned on the exposed end of the collapsible outer casing A so that the syringe is now ready for use.

As a result of the foregoing configuration, a single dose, prefilled, disposable syringe is provided which can be utilized in rapid and efficient fashion. Furthermore, the syringe is very space efficient due to the collapsible outer protective package.

Since the collapsed outer casing A does not interlock with the piston E, a second subsequent drawing of medication into the syringe 10 is prevented thereby rendering the spent syringe 10 unusable. The use of the outer casing A as both the protective cover and the syringe, allows for a smaller and more efficient packaging of the syringe.

Having described the preferred embodiment of the invention, it is believed that other modifications, variations and changes will be suggested to those skilled in the art in view of the description set forth above. It is therefore to be understood that all such variations, modifications and changes are believed to fall within the scope of the invention as defined in the appended claims.

What is claimed is:

1. A single dose, prefilled, disposable syringe comprising:
   a syringe barrel,
   a single pointed needle,
   a piston, and an outer casing,
   wherein said outer casing has an inner diameter larger than said syringe barrel in the packaged state, and wherein said outer casing surrounds said syringe barrel in said packaged state, said outer casing being collapsible to have an outer diameter smaller than an inner diameter of said syringe barrel so that said collapsed outer casing acts as a plunger to force said piston through said syringe barrel thereby ejecting said single dose of prefilled medication.

2. A single dose, prefilled, disposable syringe as recited in claim 1, wherein said outer casing is made from plastic.

3. A single dose, prefilled, disposable syringe as recited in claim 1, wherein said collapsed outer casing and said piston do not interlock, so that when said single dose of prefilled medication is ejected from said syringe, said piston cannot be withdrawn back through said barrel of said syringe by withdrawal of said collapsed outer casing.

4. A single dose, prefilled, disposable syringe comprising:
   a syringe barrel,
   a needle,
   a piston, and an outer casing,
   wherein said outer casing has an inner diameter larger than said syringe barrel in the packaged state, and wherein said outer casing surrounds said syringe barrel in said packaged state, said outer casing being collapsible to have an outer diameter smaller than an inner diameter of said syringe barrel so that said collapsed outer casing acts as a plunger to force said piston through said syringe barrel thereby ejecting said single dose of prefilled medication,
   wherein said outer casing has a plurality of longitudinal grooves formed along its outer circumference to facilitate collapsing of said outer casing.

5. A single dose, prefilled, disposable syringe as recited in claim 4, wherein said plurality of grooves are formed at equal distances around a circumference of said outer casing.

6. A single dose, prefilled, disposable syringe as recited in claim 4, wherein said plurality of grooves comprise five grooves.

7. A single dose, prefilled, disposable syringe comprising:
   a syringe barrel,
   a needle,
   a piston, and an outer casing,
   wherein said outer casing has an inner diameter larger than said syringe barrel in the packaged state, and wherein said outer casing surrounds said syringe barrel in said packaged state, said outer casing being collapsible to have an outer diameter smaller than an inner diameter of said syringe barrel so that said collapsed outer casing acts as a plunger to force said piston through said syringe barrel thereby ejecting said single dose of prefilled medication, further comprising a protective cover disposed at an end of said outer casing opposite said needle cover, wherein said protective cover is connected to said outer casing in said package state to contain said syringe.

8. A single dose, prefilled, disposable syringe as recited in claim 7, wherein said protective cover and said outer casing are connected by plastic welds, said plastic welds being breakable by application of twisting force between said protective cover and said outer casing.

9. A single dose, prefilled, disposable syringe as recited in claim 8, wherein said needle cover and said outer casing interlock with one another by flanges disposed on each of said needle cover and said outer casing, said outer casing and said needle cover being maintained in an interlocked state when said protective cover and said outer casing are connected.

10. A single dose, prefilled, disposable syringe as recited in claim 8, wherein said protective cover comprises an inner ring which fits into said barrel of said syringe in said packaged state.

11. A single dose, prefilled, disposable syringe as recited in claim 10, wherein said inner ring fits into an exposed end of said collapsed outer casing when said syringe is unpackaged and arranged for use.

12. A single dose, prefilled, disposable syringe comprising:

a syringe barrel, a needle, a piston, and an outer casing, wherein said outer casing has an inner diameter larger than said syringe barrel in the packaged state, and wherein said outer casing surrounds said syringe barrel in said packaged state, said outer casing being collapsible to have an outer diameter smaller than an inner diameter of said syringe barrel so that said collapsed outer casing acts as a plunger to force said piston through said syringe barrel thereby ejecting said single dose of prefilled medication, wherein said needle cover and said outer casing interlock with one another.

13. A single dose, prefilled, disposable syringe as recited in claim 12, wherein said needle cover and said outer casing interlock by flanges disposed on the circumference of said needle cover and said outer casing.

14. A single dose, prefilled, disposable syringe comprising:

a syringe barrel, a needle, a piston, and an outer casing, wherein said outer casing has an inner diameter larger than said syringe barrel in the packaged state, and wherein said outer casing surrounds said syringe barrel in said packaged state, said outer casing being collapsible to have an outer diameter smaller than an inner diameter of said syringe barrel so that said collapsed outer casing acts as a plunger to force said piston through said syringe barrel thereby ejecting said single dose of prefilled medication, wherein said piston has a recess for accepting said collapsed outer casing.

* * * * *